United States Patent
Palmer et al.

[11] Patent Number: 5,865,724
[45] Date of Patent: Feb. 2, 1999

[54] FLEXIBLE MICROSURGICAL INSTRUMENTS INCORPORATING A SHEATH HAVING TACTILE AND VISUAL POSITION INDICATORS

[75] Inventors: Matthew A. Palmer, Miami, Fla.; Bruce H. Diamond, Wellesley, Mass.

[73] Assignee: Symbiosis Corp., Miami, Fla.

[21] Appl. No.: 888,570

[22] Filed: Jul. 7, 1997

Related U.S. Application Data

[63] Continuation of Ser. No. 584,839, Jan. 11, 1996, abandoned.

[51] Int. Cl.$^6$ .................................................. A61B 17/28
[52] U.S. Cl. ........................ 600/104; 600/564; 606/170; 606/205
[58] Field of Search .................................... 128/751, 753, 128/754; 600/117, 104, 105, 564; 606/160, 205, 170

[56] References Cited

U.S. PATENT DOCUMENTS

| | | | |
|---|---|---|---|
| 3,964,468 | 6/1976 | Schulz ...................................... | 128/751 |
| 4,646,751 | 3/1987 | Maslanka ................................. | 128/751 |
| 4,982,727 | 1/1991 | Sato ........................................ | 600/104 |
| 5,035,248 | 7/1991 | Zinnecker ................................ | 128/751 |
| 5,217,024 | 6/1993 | Dorsey et al. ......................... | 606/160 X |
| 5,263,962 | 11/1993 | Johnson et al. ...................... | 600/117 X |
| 5,386,818 | 2/1995 | Schneebaum et al. ................. | 600/104 |
| 5,445,140 | 8/1995 | Tovey ...................................... | 600/117 |
| 5,578,056 | 11/1996 | Pauldrack ............................. | 128/751 X |

*Primary Examiner*—Michael H. Thaler
*Attorney, Agent, or Firm*—David P. Gordon; David S. Jacobson; Thomas A. Gallagher

[57] ABSTRACT

Flexible microsurgical instruments incorporating a sheath having tactile and visual position indicators are disclosed. A flexible lubricous sheath which covers at least a distal portion of the flexible coil of the instrument is provided with either contrasting colored stripes or palpable ridges, or both, which are located a predetermined distance from the distal end of the instrument. When the coil is removed from an endoscope, the practitioner or the assistant observes the coil as it is withdrawn and notices the appearance of the stripes as an indication that the distal end of the instrument is not far away. Upon observing the stripes, the practitioner or the assistant may then slowly remove the remainder of the coil to avoid whipping the distal end as it exits the endoscope. Alternatively, the practitioner or assistant may grasp the coil between a thumb and fingers to feel for the palpable ridges as the coil is withdrawn from the endoscope or feel for vibration of the coil as the textured portion exits the endoscope. Preferred aspects of the invention include: covering the entire flexible coil with the sheath, locating the indicator (s) approximately eight to ten inches from the distal end of the instrument, applying the tactile indicator by hot stamping the sheath and applying the visual indicator with pigment bearing polymeric based tape.

10 Claims, 2 Drawing Sheets

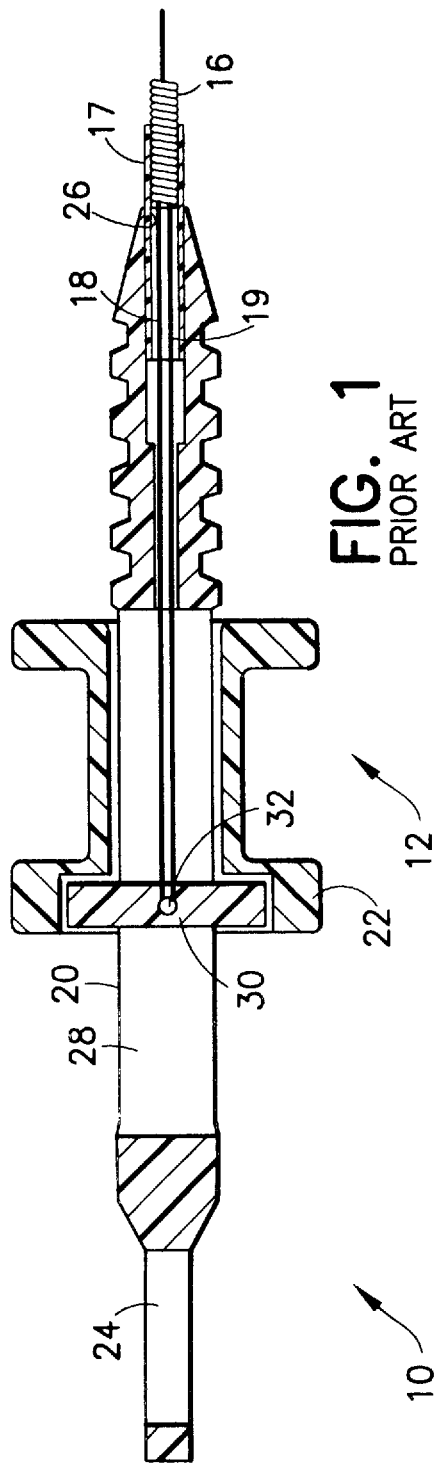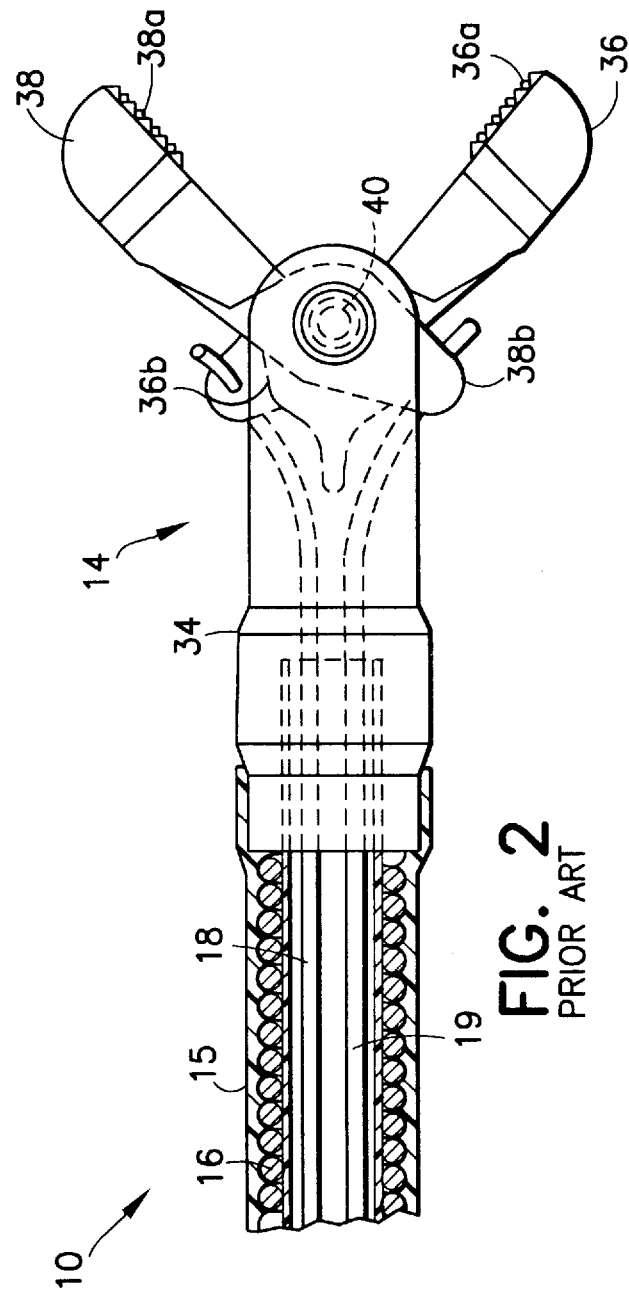

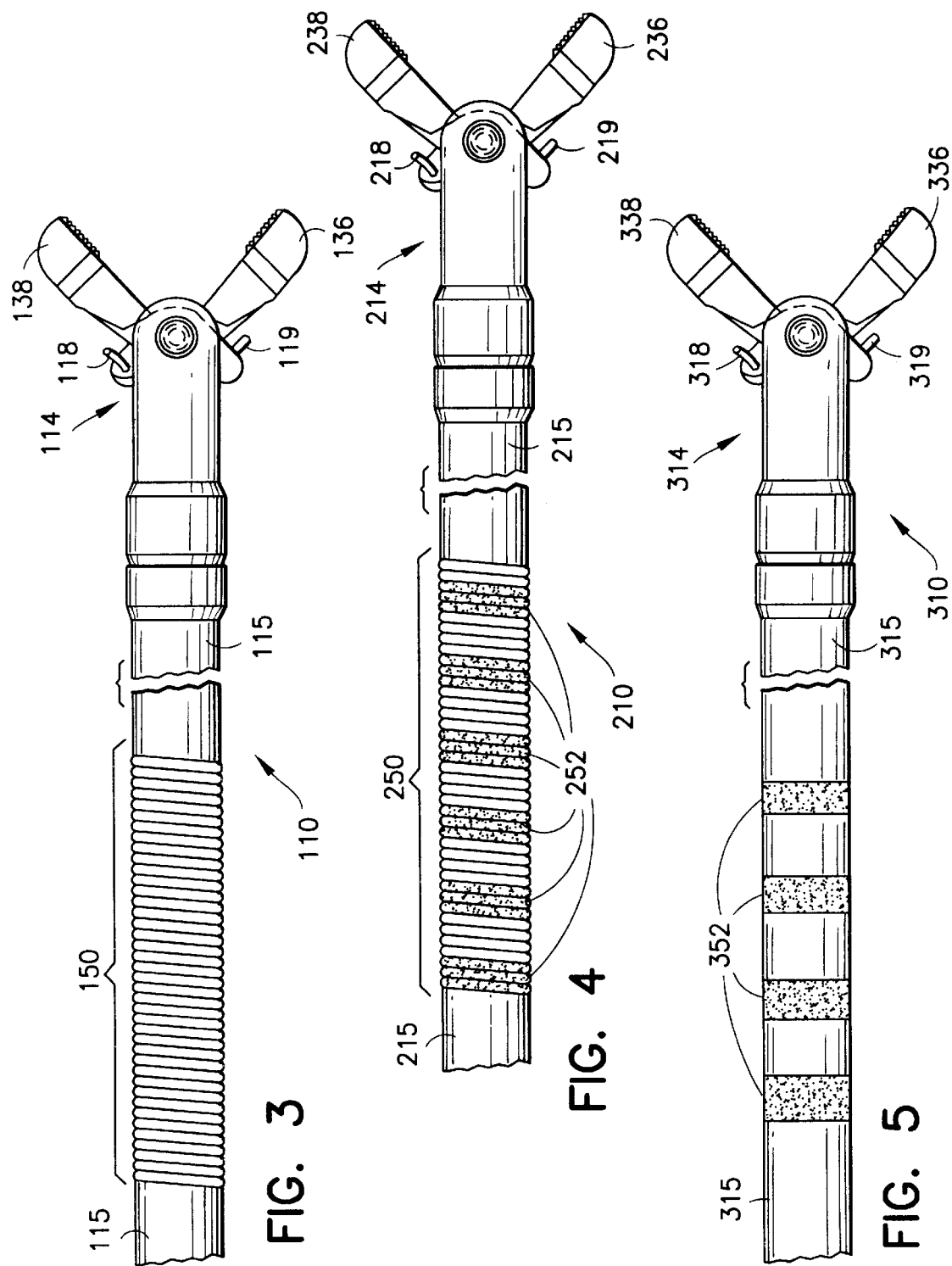

FLEXIBLE MICROSURGICAL INSTRUMENTS INCORPORATING A SHEATH HAVING TACTILE AND VISUAL POSITION INDICATORS

This is a continuation of application, Ser. No. 08/584,839, filed Jan. 11, 1996, now abandoned.

BACKGROUND OF THE INVENTION

1. Field of the Invention

The invention relates to flexible microsurgical instruments. More particularly, the invention relates to a sheath which covers the flexible coil of a flexible microsurgical instrument and which has a tactile and a visual position indicator.

2. State of the Art

Flexible microsurgical instruments, in particular endoscopic biopsy forceps, are used for taking tissue samples from the human body for analysis. These instruments typically have a long (e.g. 8 feet) flexible coil containing one or more control wires coupled to a proximal actuating handle. The actuating handle moves the control wires relative to the coil to effect a tissue sampling operation at the distal end of the coil. A pair of forceps jaws are mounted on a clevis at the distal end of the coil. The forceps jaws are coupled to the control wires so that movement of the control wires causes the jaws to open and close to bite a tissue sample.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. While viewing the biopsy site through the optical lens of the endoscope, the practitioner manipulates the actuating handle to effect a tissue sampling operation at the distal end of the instrument. After a sample has been obtained, the practitioner and/or an assistant carefully withdraws the instrument from the endoscope while holding the actuating handle to maintain the jaws in a closed position lest the sample be lost inside the endoscope. The flexible coil of the instrument is "springy" and subject to a whip-like behavior as the jaws of the instrument are withdrawn from the endoscope. If the coil is withdrawn from the endoscope too quickly, the jaws of the instrument will be whipped through the air as they exit the endoscope and result in the possible loss or contamination of the biopsy sample. Therefore, the practitioner and/or the assistant must be very careful in withdrawing the flexible coil of the instrument to be aware of when the jaws will exit the endoscope.

SUMMARY OF THE INVENTION

It is therefore an object of the invention to provide a means for indicating the position of biopsy forceps jaws inside an endoscope.

It is also an object of the invention to provide both visual and tactile indication of the position of biopsy forceps jaws inside an endoscope.

It is another object of the invention to provide means for indicating the position of biopsy forceps jaws inside an endoscope which does not interfere with the operation of the biopsy forceps or the endoscope.

It is still another object of the invention to provide means for indicating the position of biopsy forceps jaws inside an endoscope which is easy to use.

It is also an object of the invention to provide means for indicating the position of biopsy forceps jaws inside an endoscope which is inexpensive to manufacture.

In accord with these objects which will be discussed in detail below, the present invention includes a flexible lubricous sheath which covers at least a distal portion of the flexible coil of a flexible microsurgical instrument. The sheath is provided with either a series of contrasting colored stripes or a series of palpable ridges, or both, which are located a predetermined distance from the distal end of the microsurgical instrument. When the flexible coil of the microsurgical instrument is removed from an endoscope, the practitioner or the assistant observes the flexible coil as it is withdrawn and notices the appearance of the stripes on the sheath as an indication that the distal end of the instrument is not far away. Upon observing the stripes, the practitioner or the assistant may then slowly remove the remainder of the coil to avoid whipping the distal end as it exits the endoscope. Alternatively, the practitioner or assistant may grasp the coil between a thumb and fingers to feel for the palpable ridges as the coil is withdrawn from the endoscope. The ridges may also create a vibration or an audible sound and they pass through the proximal end of the endoscope.

Preferred aspects of the invention include: covering the entire flexible coil with the sheath, fabricating the sheath from HDPE or TEFLON, including both a visual and a tactile indicator, and locating the indicator approximately eight to ten inches from the distal end of the instrument. The presently preferred method of applying the tactile indicator is by hot stamping the sheath so that it acquires the texture of the underlying coil. The presently preferred method of applying the visual indicator is with two pieces of polymeric based pigment bearing tape which are placed on the sheath prior to using a hot stamping machine. Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of the proximal end of a prior art endoscopic biopsy forceps instrument;

FIG. 2 is an enlarged broken side elevation view in partial section of the distal end of a prior art endoscopic biopsy forceps instrument;

FIG. 3 is an enlarged broken side elevation view of the distal end of an endoscopic biopsy forceps instrument according to a first embodiment of the invention;

FIG. 4 is an enlarged broken side elevation view of the distal end of an endoscopic biopsy forceps instrument according to a second embodiment of the invention; and FIG. 5 is an enlarged broken side elevation view of the distal end of an endoscopic biopsy forceps instrument according to a third embodiment of the invention.

DETAILED DESCRIPTION OF THE PREFERRED EMBODIMENTS

Referring now to FIGS. 1 and 2, a known endoscopic biopsy forceps instrument 10, suitable for use with the present invention, generally includes a proximal handle 12 and a distal end effector assembly 14. A long flexible coil 16 having a pair of axially displaceable control wires 18, 19 extending therethrough couples the handle 12 and the end effector assembly 14. The coil 16 is preferably covered with a PTFE, FEP or polyolefin sheath 15 along substantially all of its length and a strain relief sleeve 17 covering a portion of the coil which extends from the handle 12. The control wires 18, 19 are preferably flexible but longitudinally inelastic and is ideally formed from 304 Steel and provided with an outer diameter of approximately .018 inch. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a coupling means 32 for attaching the proximal ends of the control wires 18, 19. The end effector assembly 14 includes a clevis 34 which is coupled to the distal end of the coil 16, and a pair of forceps jaws 36, 38 which are rotatably mounted in the clevis 34 by means of an axle pin 40. Each jaw 36, 38 is provided with distal cutting teeth 36a, 38a and a proximal tang 36b, 38b. The proximal tangs 36b, 38b are each coupled to the distal end of a respective control wire 18, 19.

From the foregoing, those skilled in the art will appreciate that relative movement of the shaft 20 and spool 22 results in movement of the control wires 18, 19 relative to the coil 16. Such action results in opening and closing of the jaws 36, 38.

Turning now to FIG. 3, a flexible lubricous sheath 115 according to the invention is shown in conjunction with the distal end of a biopsy forceps instrument 110 which is otherwise substantially the same as the known instrument 10 described above and where similar reference numerals refer to similar parts of the instrument. According to a first embodiment of the invention, the flexible lubricous sheath 115 is provided with a palpable texture 150 which is located a defined distance from the end effector assembly 114. The presently preferred method of applying the texture 150 to the sheath 115 is by hot pressing the sheath 115 so that it acquires the texture of the underlying coil (16 in FIG. 1). The presently preferred location of the texture 150 is approximately eight to ten inches from the end effector assembly 114. It is preferable that the texture (tactile indicators) not be located any closer to the end effector assembly so that they do not exit the distal end of the endoscope and possibly interfere with the positioning of the end effectors at the biopsy site.

Referring now to FIG. 4, a flexible lubricous sheath 215 according to a second embodiment of the invention is shown in conjunction with the distal end of a biopsy forceps instrument 210 which is otherwise substantially the same as the known instrument 10 described above and where similar reference numerals refer to similar parts of the instrument. According to the second embodiment of the invention, the flexible lubricous sheath 215 is provided with a palpable texture 250 and a visible marking such as color contrasting lines 252 which are located a defined distance from the end effector assembly 214. The presently preferred method of applying the color contrasting lines 252 to the sheath 215 is by applying a pigment bearing polymeric based tape to the sheath 215 prior to hot pressing the pigment bearing tape and the sheath 215 so that the sheath acquires the texture of the underlying coil (16 in FIG. 1). The heat of the hot press not only causes the sheath to acquire the texture of the underlying coil, but transfers the pigment from the tape to the sheath. The pigment layer on the tape is preferably less than 0.001 inches thick, and approximately three inches wide. Using a hot press die having fingers approximately one-eighth inch wide and spaced three-eighths of an inch apart, six or seven spaced one-eighth inch bands of pigment from the three inch pigment bearing tape will be transferred to the sheath. Typically, the sheath 215 will be one of several colors such as black, white, orange, yellow, blue, or red, and the pigmented lines 252 will be a contrasting color such as black or white depending on the color of the sheath. It will also be understood that the visible marking need not be lines (rings), but could be any other easily visible marking such as a helix, hatch marks, or a single stripe or patch, etc. According to this second embodiment of the invention, the texture 250 and the visible marking 252 are preferably located at approximately the same position on the sheath 215; i.e., the textured portion of the sheath bears the visible markings. However, it is possible to locate the visible markings apart from the textured portion.

Turning now to FIG. 5, a flexible lubricous sheath 315 according to a third embodiment of the invention is shown in conjunction with the distal end of a biopsy forceps instrument 310 which is otherwise substantially the same as the known instrument 10 described above and where similar reference numerals refer to similar parts of the instrument. According to the third embodiment of the invention, the flexible lubricous sheath 315 is provided with a visible marking such as color contrasting lines 352 which are located a defined distance from the end effector assembly 314. The markings 352 may be applied to the sheath 315 prior to covering the coil (16 in FIG. 1) with the sheath. Typically, the sheath 315 will be one of several colors as mentioned above and the markings 352 will be a contrasting color such as black or white depending on the color of the sheath. It will also be understood that the visible marking need not be lines (rings), but could be any other easily visible marking such as a helix, hatch marks, or a single stripe or patch, etc.

There have been described and illustrated herein several embodiments of a flexible microsurgical instrument incorporating a flexible sheath having tactile and visual position indicators. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

We claim:

1. A flexible endoscopic instrument for insertion through the lumen of an endoscope, comprising:

a) a unitary flexible coil having a proximal end and a distal end;

b) at least one control wire having a proximal end and a distal end, said at least one control wire extending through said flexible coil and being axially displaceable relative to said coil;

c) a proximal actuator coupled to said proximal end of said flexible coil and said proximal end of said at least one control wire for effecting an axial displacement of said at least one control wire relative to said coil;

d) an end effector assembly coupled to said distal end of said flexible coil and said distal end of said at least one control wire; and e) a flexible lubricous sheath covering at least a distal portion of said flexible coil, said sheath including a proximal end, a distal end and at least one of visual indicia and palpable indicia spaced at least a few inches from said end effector assembly, said indicia indicating a location which is a predetermined distance from said end effector assembly, and which is closer to said end effector assembly than to said proximal actuator.

2. A flexible endoscopic instrument according to claim 1, wherein:

said visual indicia comprises a plurality of stripes.

3. A flexible endoscopic instrument according to claim 1, wherein:

said palpable indicia comprises a textured portion of said sheath.

4. A flexible endoscopic instrument according to claim 3, wherein:

said textured portion is formed by hot pressing a portion of said sheath onto said flexible coil.

5. A flexible endoscopic instrument according to claim 1, wherein:

said at least one of visual indicia and palpable indicia is spaced approximately eight to ten inches proximal of said end effector assembly.

6. A flexible endoscopic instrument according to claim 1, wherein:

said sheath covers substantially the entire length of said flexible coil.

7. A flexible endoscopic instrument according to claim 1, wherein:

said sheath includes both visual indicia and palpable indicia spaced proximally of said end effector assembly.

8. A flexible endoscopic instrument according to claim 7, wherein:

said visual indicia comprises a plurality of stripes.

9. A flexible endoscopic instrument according to claim 7, wherein:

said palpable indicia comprises a textured portion of said sheath.

10. A flexible endoscopic instrument according to claim 7, wherein:

said visual indicia and said palpable indicia are formed by covering a portion of said sheath with a pigment bearing polymeric tape and hot pressing said portion of said sheath onto said flexible coil.

* * * * *

UNITED STATES PATENT AND TRADEMARK OFFICE
CERTIFICATE OF CORRECTION

PATENT NO. : 5,865,724
DATED : February 2, 1999
INVENTOR(S) : Matthew A. PALMER et al.

It is certified that error appears in the above-indentified patent and that said Letters Patent is hereby corrected as shown below:

On the title page,

In the Abstract, Item [57], lines 19 and 20, "indicator" and "(s)" should be on the same line.

In Claim 1, Col. 4, line 49, delete "unitary".

Signed and Sealed this

Twenty-fifth Day of May, 1999

Attest:

Q. TODD DICKINSON

Attesting Officer

Acting Commissioner of Patents and Trademarks